(12) United States Patent
Boeh et al.

(10) Patent No.: US 7,834,336 B2
(45) Date of Patent: Nov. 16, 2010

(54) TREATMENT OF PATIENT TUMORS BY CHARGED PARTICLE THERAPY

(75) Inventors: Lester D. Boeh, Belmont, CA (US); James Clayton, Sarotoga, CA (US); Marcel R. Marc, San Jose, CA (US); Armin Langenegger, Las Vegas, NV (US)

(73) Assignee: Varian Medical Systems, Inc., Palo Alto, CA (US)

( * ) Notice: Subject to any disclaimer, the term of this patent is extended or adjusted under 35 U.S.C. 154(b) by 239 days.

(21) Appl. No.: 12/128,500

(22) Filed: May 28, 2008

(65) Prior Publication Data

US 2009/0296885 A1    Dec. 3, 2009

(51) Int. Cl.
*A61N 5/00* (2006.01)
*H05H 13/00* (2006.01)
*G21K 1/02* (2006.01)

(52) U.S. Cl. .................. 250/505.1; 250/398; 250/492.3; 315/500; 315/503; 378/65

(58) Field of Classification Search .............. 250/505.1, 250/398, 492.3; 378/65; 315/500, 503
See application file for complete search history.

(56) References Cited

U.S. PATENT DOCUMENTS

| | | | |
|---|---|---|---|
| 5,668,371 A * | 9/1997 | Deasy et al. ............... | 850/1 |
| 6,992,312 B2 | 1/2006 | Yanagisawa et al. | |
| 7,212,609 B2 | 5/2007 | Nagamine et al. | |
| 7,242,742 B2 | 7/2007 | Calderon et al. | |
| 7,247,869 B2 | 7/2007 | Tadokoro et al. | |
| 2008/0067405 A1 * | 3/2008 | Nihongi et al. ............. | 250/398 |
| 2010/0051833 A1 * | 3/2010 | Guertin et al. ........... | 250/515.1 |

OTHER PUBLICATIONS

PCT, International Search Report and Written Opinion of the International Searching Authority in PCT/US2009/045193, Jan. 11, 2010, 13 pages.
Karl Otto, "Volumetric modulated arc therapy: IMRT in a single gantry arc," Medical. Physics. vol. 35, No. 1, Jan. 2008, pp. 310-317.
Varian Medical Systems, Inc., "Varian Proton Therapy System," Jul. 2007, 7 pages.
Varian Medical Systems, Inc., "Rapid Arc. One revolution is all it takes," Oct. 2007, 7 pages.
Leavitt, "Electron Arc Therapy Dosimetry and Treatment Planning," Proceedings Ninth Varian Clinac Users Meeting, May 9-11, 1982, pp. 6-11.
Leavitt, "Multileaf Collimation in Electron Arc Therapy," Proceedings Twelfth Varian Clinac Users Meeting, May 1-3, 1988, pp. 63-67.

* cited by examiner

*Primary Examiner*—Nikita Wells
(74) *Attorney, Agent, or Firm*—Houst Consulting

(57) ABSTRACT

A method of irradiating a target in a subject using charged particle therapy includes the steps of positioning a subject on a supporting device, positioning a delivery device adapted to deliver charged particles, and delivering charged particles to a target in the subject wherein the delivery device rotates around the target during delivery of at least a portion of the charged particles.

30 Claims, 3 Drawing Sheets

US 7,834,336 B2

TREATMENT OF PATIENT TUMORS BY CHARGED PARTICLE THERAPY

TECHNICAL FIELD

This invention relates in general to radiation treatment of disease and in particular to systems and methods for treating patients with tumors using charged particle therapy.

BACKGROUND

Particle therapy systems and methods are known for treating patients with tumors. In particle therapy, charged particles such as protons or heavy ions are used as the source of radiation. Because of the "Bragg peak" effect, charged particles release most of their energy around the area where they stop. Therefore, by choosing the energy of charged particles, the healthy tissue or critical organs distal to the radiation source with respect to the tumor receives no radiation, and the healthy tissue proximal to the Bragg peak receives a significantly reduced amount of radiation.

To make particle therapy available to a large population, it is necessary to develop an optimal delivery system that requires minimal patient setup and treatment time, and that has the capability to produce conformal dose distributions with a higher degree of precision than is currently available. Conformal dose delivery maximizes the radiotherapy dose to the tumor region while minimizing the dose delivered to the surrounding healthy tissue and spares other critical organs. Current particle therapy systems use static fields, which add to patient treatment times. Such systems also compromise the conformity of the delivered dose such that critical organs or more non-cancerous tissue are exposed to unnecessary radiation of treatment beam. The high cost of particle therapy systems challenge the providers to develop optimal systems that meet the goals of conformal delivery of radiation to target tumors with minimal treatment time.

SUMMARY

A method of irradiating a target in a subject using charged particle therapy is provided. The method comprises the steps of positioning a subject on a supporting device, positioning a delivery device adapted to deliver charged particles, and delivering charged particles to a target in the subject wherein the delivery device rotates around the target during delivery of at least a portion of the charged particles.

In the provided method, one or more parameters of the charged particles may be modulated during the rotation of the delivery device. The parameters include but are not limited to the energy, the intensity, the beam direction, and the beam shape of the charged particles.

In a preferred embodiment, all or substantially all of the charged particles for a treatment fraction are delivered to the target during a single rotation of the delivery device in about 360 degrees or less.

In some embodiments, the energy, the intensity, the beam direction, and the beam shape of the charged particles are concurrently modulated during the rotation of the delivery device. A multi-leaf collimator such as a 3-dimensional (3D) multi-leaf collimator may be used to shape and modulate the energy of the charged particles concurrently.

In some embodiments, the delivery device is mounted to a gantry capable of rotating in 360 degrees or more. In some embodiments, the patient supporting device is movable.

In another method provided by the invention, a subject is positioned on a supporting device. A delivery device is positioned to deliver charged particles to a target in the subject. The delivery device rotates around the target during delivery of at least a portion of the charged particles. The energy of the charged particle beam is modulated during the rotation of the delivery device such that the Bragg peaks of the particle beam are deposited primarily on the distal periphery of the target during the delivery of the particle beam during rotation.

In some embodiments, the delivery device is stationary during delivery of at least a portion of the charged particles. In a preferred embodiment, the charged particles are in the form of a pencil beam. The charged particles may be protons or heavier ions.

In some embodiments, the charged particles for a treatment fraction are delivered to a target in the subject using a delivery device with two rotations. In a first rotation, the Bragg peaks of substantially all charged particles are deposited primarily on the distal periphery of the target. In a second rotation, the Bragg peaks of substantially all charged particles are deposited primarily in the interior of the target volume. Each of the two rotations can be in about 360 degrees or in any degree less than 360 degrees.

In another aspect, a charged particle therapy system is provided. The system includes a particle accelerator, a particle beam delivery device, a beam path adapted to transport charged particles generated from the particle accelerator to the beam delivery device. The beam delivery device is adapted to rotate around a target during delivery of at least a portion of charged particles to the target in operation.

In some preferred embodiments, the delivery device is coupled to a gantry rotatable in 360 degrees or more.

In some embodiments, the delivery device comprises a multi-leaf collimator such as a 3D multi-leaf collimator. The multi-leaf collimator may be configured to shape and modulate the energy of the charged particles concurrently. The multi-leaf collimator may also be configured to shape and scatter the charged particles concurrently.

BRIEF DESCRIPTION OF THE DRAWINGS

These and various other features and advantages of the present invention will become better understood upon reading of the following detailed description in conjunction with the accompanying drawings and the appended claims provided below, where:

DETAILED DESCRIPTION OF VARIOUS EMBODIMENTS

Figure 1:
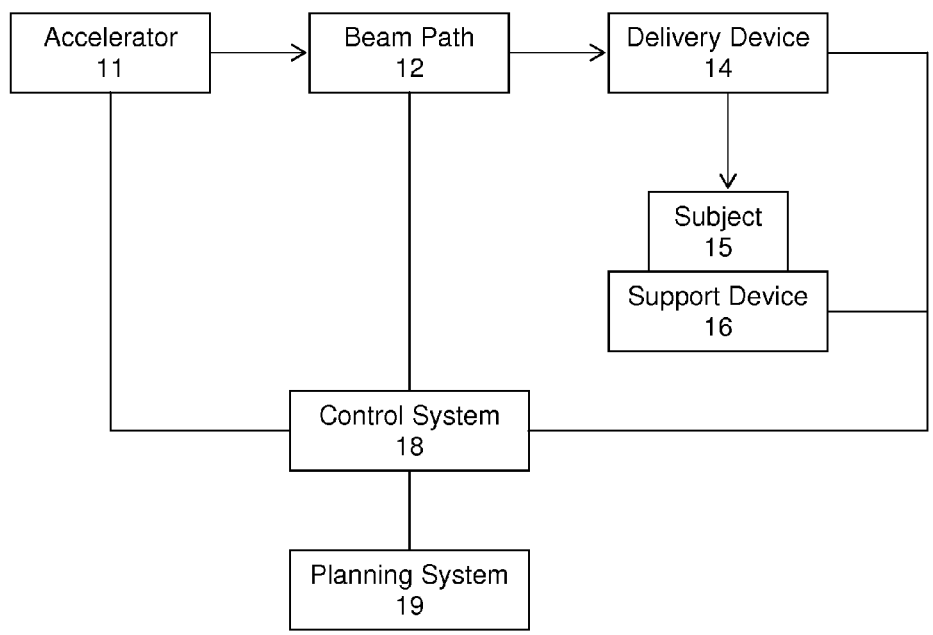
FIG. 1 is a block diagram illustrating a charged particle therapy system in accordance with one embodiment of the invention.

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments of the invention.

In general, the invention provides a method of treating patient tumors using charged particle therapy. Charged particles for a treatment fraction can be delivered to a tumor using a particle beam delivery device with one rotation of 360 degrees or less around the tumor. The energy of the charged particles can be selected such that the Bragg peaks of the charged particles are deposited primarily on the distal periphery of the tumor. Alternatively, the charged particles for a treatment fraction can be delivered using a particle delivery device with two rotations. Each of the two rotations can be in about 360 degrees or less. In a first rotation, the Bragg peaks of the charged particles may be deposited primarily on the distal periphery of the tumor volume. In a second rotation the Bragg peaks of the charged particles may be deposited primarily in the interior of the target volume. One or more parameters of the particle beam including the intensity, the energy, the shape and size of the particle beam, and the radiation time in any position may be modulated or controlled based on an optimized treatment plan to deliver a conformal dose to the tumor site. It is also possible to adjust or control the patient position during the treatment by adjusting the patient supporting device. The charged particle therapy system and method provided by the invention significantly reduce treatment time and improve dose conformity.

As used herein, the term "charged particles" refer to electrons, protons or heavy ions such as ions of helium, carbon, neon, argon, or other charged elemental particles.

FIG. 1 is a block diagram illustrating a charged particle therapy system 10 in accordance with some embodiments of the invention. The charged particle therapy system 10 includes a particle accelerator 11, a beam path 12, and a beam delivery device 14. A subject 15 such as a patient to be treated is supported on a supporting device 16 such as a treatment couch or chair. A treatment control system 18 receives and executes a patient treatment plan provided by a treatment planning system 19. The control system 18 generates signals to the particle accelerator 11, beam path 12, beam delivery device 14, and supporting device 16 based on the patient treatment plan. The operations of the particle accelerator 11, beam path 12, beam delivery device 14, and/or the supporting device 16 are controlled such that the parameters of the charged particles including the energy, the intensity, the direction, and the size and/or shape of the beam are dynamically modulated or controlled during the treatment based on the patient treatment plan.

The particle accelerator 11 is a source of charged particles such as electrons, protons or heavy ions such as ions of helium, carbon, neon, argon, or other charged elemental particles. The energy of the charged particles may be greater than 20, 50, 70, 100, 250 or 500 MeV depending on specific applications. The particle accelerator 11 may be a cyclotron, synchrotron, linear accelerator, or any other accelerators configured to accelerate charged particles. Cyclotrons, synchrotrons, and linear accelerators are known in the art. In general, a cyclotron uses dipole magnets and the magnetic field produced by an oscillating voltage to accelerate charged particles. Generally, the size of the magnets and the strength of the magnetic fields control the energy of charged particles generated by a cyclotron. The energy of the charged particle beams generated by cyclotrons can be 100, 250, 500 MeV or higher. The intensity of the particle beams generated by cyclotrons may be controlled by means such as slits that are generally used to limit the ion source. Cyclotrons extract particles with a fixed energy for clinical purposes. Thus an energy modification system is generally needed in the beam path. The energy modification system may include energy degraders of variable thickness to intercept the particle beam, e.g., wedges that can be moved in and out of the beam quickly. Synchrotrons use a circular accelerator ring and electromagnetic resonant cavities around the ring to accelerate particles. Synchrotrons deliver pulsed beams, i.e. they accelerate and extract ions with a specific repetition rate. Synchrotrons may produce particle beams with a variety of energies as compared to cyclotrons which typically generate fixed extraction energy. Thus synchrotrons allow beam extraction for any suitable energy. By way of example, the energy of particle beams extracted from synchrotrons may be up to 100, 250 or 500 MeV or higher. In linear accelerators (Linac), particles are accelerated in a straight line with a target of interest at one end. Linear accelerators may be used to produce charged particle beams with energy ranging from 6 to 60 MeV or higher. They are also used with cyclotrons or synchrotrons to provide an initial low-energy kick to particles before they are injected to the circular accelerators.

The beam path 12 transports the charged particle beams extracted from the particle accelerator 11 to the beam delivery device 14 in a treatment room. One or more beam paths 12 may be used to transport charged particles from the particle accelerator 11 to one or more treatment rooms. Bending magnets (not shown) may be used to steer the particle beam from the particle accelerator 11 to the beam delivery device 14. The beam path 12 may include energy modification components (not shown) such as energy degraders configured to modify the energy of the particle beam extracted from the particle accelerator 11. The energy degrader may be made of high or low atomic number materials. The beam path 12 may further include slits to adjust or modify the intensity of the particle beams extracted from the particle accelerator 11.

The beam delivery device or nozzle 14 contains various components for beam modulation, shaping, and monitoring. In some embodiments, the beam delivery device 14 may be mounted to a gantry capable of rotating around the target in 360 degrees. Depending on applications, the beam delivery device 14 may include energy modifiers, scatterers or scattering media, wobbling or scan magnets, beam monitors, collimators, compensators, and other components configured to modulate the parameters of the particle beam to be delivered to the target 15.

Figure 2A:
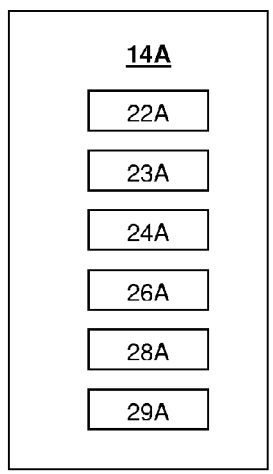
FIG. 2A is a block diagram illustrating a particle beam delivery device in accordance with one embodiment of the invention.

FIG. 2A is a block diagram illustrating a beam delivery device 14A in accordance with one embodiment of the invention. The use of single or double scatterers in combination with other components provides a broad uniform modulated particle beam. In a preferred embodiment, the beam delivery device 14A includes scatterers 22A, 23A, energy modifiers 24A, beam monitors 26A, collimators 28A, and compensators 29A.

The scatterers 22A, 23A broaden the particle beam and/or ensure a uniform beam profile. For small field radiation, a single scattering foil may be used to broaden the beam. For large field radiation, a double-scattering system may be used to ensure a broad uniform beam profile. For example, in a double-scattering system, a first scatter 22A may be placed upstream near the entrance of the beam delivery device 14A, and a second scatter 23A may be placed further downstream.

The energy modifiers 24A are configured to modify the energy of the beam such that the beam range within the targeted tumor is controlled. The energy modifiers 24A can be made of suitable energy absorbing materials such as carbon (a low-Z material), lead (a high-Z material) or other suitable materials. The energy modifiers 24A may be in various forms including shifters, wheels, wedges, or filters. By varying the thickness and/or form of the energy absorbing materials, the beam energy can be modified in a time and/or spatial dependent manner. For example, a spread-out Bragg peak (SOBP) filter is a range modulator made of energy absorbing materials of variable thickness. By sequentially passing the beam through the energy absorbing material of variable thickness, the Bragg peaks are spread out along the depth of the target volume.

Beam monitors 26A are used to monitor the beam parameters. The beam monitors 26A include means for measuring the energy, intensity or dose rate, and uniformity of the particle beam. The beam monitors 26A output signals representing the beam parameters information to the control system 18, which is provided with predetermined values for the beam parameters. The control system 18 processes the measured signals and provides control signals for operation of beam delivery device 14.

Collimators 28A are used to shape and/or size the beam to a desired profile. The collimators 28A may be fixed apertures that are custom made of suitable materials such as plastics or brass. In some embodiments, the collimators 28A are dynamic multi-leaf collimators. In some preferred embodiments, the collimators 28A are 3D multi-leaf collimators. For example, a multi-leaf collimator may include a plurality of pairs of opposing veins or leaves made of materials that effectively block the particle beam. Each pair of the leaves is controllably movable relative to each other. By driving each leaf into different positions, the size and shape of the particle beam can be controlled and a desired target profile is formed.

The number of leaves in a multi-leaf collimator can have a wide range. Generally, a multi-leaf collimator having a large number of narrow leaves has a higher resolution than a multi-leaf collimator having a small number of wider leaves. A high resolution is generally beneficial in shaping the radiation beam precisely to the shape of the tumor and modulating the radiation intensity precisely.

In some embodiments, the collimators 28A may include more than one multiple leaf collimators, with one collimator superimposed over another collimator. The multiple leaves in one collimator can be at an angle, e.g., 45 or 90 degrees with respect to the multiple leaves in another collimator. Such an arrangement of more than one multi-leaf collimator superimposed over each other allows shaping of the radiation beam in more diverse shapes.

In some embodiments, the materials and/or thicknesses of the MLC leaves may be chosen such that the energy of the particle beam passing through the multi-leaf collimator may be modified. As such, the MLC may perform the functions of both beam shaping and beam energy modulation. This is advantageous because energy modulation by MLC may be quicker as compared to that by changing particle accelerator parameters. As a result, the need for changing accelerator parameters for beam energy modulation may be eliminated during the rotation of the beam delivery device 14.

In some embodiments, the materials of MLC leaves may contain scattering media so that the collimator may also perform the function of scatterers.

Compensators (or bolus) 29A are range modulators that are tailored to the individual patient based on the position of the tumor and the anatomic situation of the patient and can be used to shape the beam distally. The combination of the energy modifiers 24A and the custom-made compensator 29A ensures to spare the surrounding health tissue and organs at risk at the distal edge of the treated target volume.

Figure 2B:
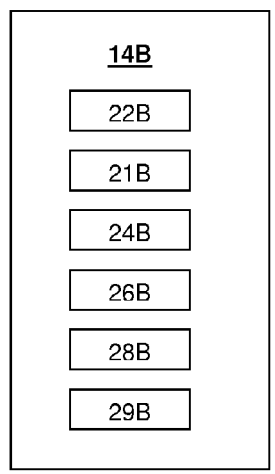
FIG. 2B is a block diagram illustrating a particle beam delivery device in accordance with another embodiment of the invention.

FIG. 2B is a block diagram illustrating a beam delivery device 14B in accordance with another embodiment of the invention. The use of wobbling magnets 21B provides a broad, uniform particle beam profile. In a preferred embodiment, the beam delivery device 14B includes wobbling magnets 21B, energy modifiers 24B, beam monitors 26B, collimators 28B, compensators 29B, and optionally scatterers 22B.

The wobbling magnets 21B include a pair of vertical and horizontal magnets. The beam is actively deflected by the pair of dipole magnets. For example, the produced sinusoid fields can be phase shifted by 90 degrees so that ring shaped fields are formed. The superposition of a series of rings sums up to homogeneous covering fields. Optionally, one or more scatterers 22B may be used in combination with wobbling magnets 21B to provide a broader uniform beam profile. In some preferred embodiments, the driver for magnetic current is a saw tooth wave form.

Figure 2C:
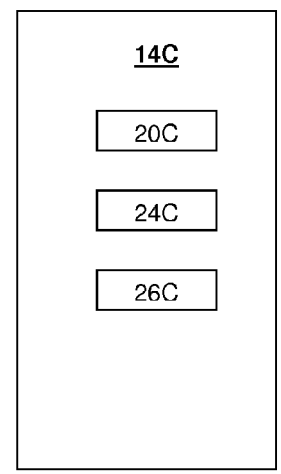
FIG. 2C is a block diagram illustrating a particle beam delivery device in accordance with a further embodiment of the invention.

FIG. 2C is a block diagram illustrating a beam delivery device 14C in accordance with a further embodiment of the invention. In comparison with the beam delivery devices 14A, 14B illustrated in FIGS. 2A and 2B, vertical and horizontal scanning magnets 20C are used to fast scan a pencil beam over a target. In some embodiments, the pencil beam may be continuously moved along predetermined scan-lines over a target (raster scan). In some embodiments, the pencil beam may be switched off and on in a predetermined time interval when moving from one spot to another (spot scanning). The intensity of the beam is controlled to ensure each target spot receives a desired dose. In the case of raster scanning, the velocity of the pencil beam may be adjusted to the desired dose. In the case of spot scanning, the spot dwelling time may be adjusted to the desired dose. The intensity of the pencil beam may be controlled or adjusted by controlling the particle accelerator and/or the slits disposed along the bean path.

In some embodiments, the particle beam may scan (either raster scan or spot scan) over the whole area of a slice of the target volume. The energy of the beam may be selected such that the Bragg peaks of the scan are deposited on the slice. By modulating the energy of the beam, the whole volume of the target can be uniformly irradiated layer by layer.

In some embodiments, the beam energy is selected such that the Bragg peaks of the beam are deposited on the distal periphery edge of the target volume. The combined effect of the periphery deposition of Bragg peaks provides a desired uniform dose in the interior of the target volume. In some preferred embodiments, the beam energy is continuously modulated while the beam delivery device rotates around the target such that the Bragg peaks of the beam are deposited over the periphery of the target volume.

By way of example, the periphery edge of the target volume may be scanned or continuously scanned by rotating the beam delivery device 14, or a gantry to which the beam delivery device 14 is mounted, around the target volume. Alternatively, the periphery edge of the target volume may be scanned or continuously scanned by rotating the supporting device 16 on which the patient is supported. As such, the supporting device 16 may be moved in multiple degrees of freedom, including motions in translational and/or rotational directions. The supporting device 16 may be mounted to an articulated arm which is capable of rotating and/or translating in multiple degrees of freedom. In some embodiments, the periphery of the target volume is scanned or continuously scanned by rotating the beam delivery device 14 and moving the patient supporting device 16 concurrently. In some preferred embodiments, the gantry to which the delivery device 14 is mounted is configured to be capable of rotating in 360 degrees or more.

In some embodiments, the charged particles for a treatment fraction may be delivered to a tumor using the delivery device 14 with a single rotation. The rotation may be a complete rotation in about 360 degrees or a partial rotation in any degree less than 360 degrees such as 45, 90, 180, 270, or 330 degrees, for example. The rotation of the delivery device 14 may be continuous during which the charged particles are delivered to the target. Alternatively, the rotation may be non-continuous or may operate in an alternating mode of rotation, stop, and rotation. Charged particles may be delivered to a target when the delivery device 14 rotates, or when the delivery device 14 is stationary. For example, the delivery of charged particles for a treatment fraction may be carried out at discrete or selected angles during partial or complete rotation. One or more of the parameters of the charged particles including the energy, the intensity, the beam direction, or the beam shape may be modulated or concurrently modulated during the rotation or pause of the delivery device 14.

In some embodiments, the charged particles for a treatment fraction may be delivered to a tumor using the delivery device 14 with more than one rotation such as two rotations. In a first rotation, at least the energy of the charged particles is modulated such that the Bragg peaks of substantially all charged particles are deposited primarily on the distal periphery of the tumor. In a second rotation, the energy of the charged particles is modulated such that the Bragg peaks of substantially all charged particles are deposited primarily in the interior of the tumor volume. The intensity, beam direction, or beam shape may also be modulated during each of the two rotations. Each of the first and second rotations may be a complete rotation in about 360 degrees or a partial rotation less than 360 degrees. The delivery of the charged particles may be carried out during either rotation or pause of the delivery device 14.

Returning to FIG. 1, the treatment control system 18 controls the operation of the particle treatment system 10. The control system 18 receives, stores, and executes a treatment plan established in a pre-treatment planning session. The control system 18 includes a controller comprising a signal processor such as, for example, a digital signal processor (DSL), a central processing unit (CPU), or a microprocessor (μP), and a memory coupled to the signal processor. The memory serves to store a treatment plan for the patient and other programs for the operation of the particle beam treatment system 10. Based on the treatment plan, the controller executes the program and generates signals for operation of the particle accelerator 11, beam path 12, delivery device 14 or individual components in the delivery device 14, and patient's support device 16. Responsive to the signals from the control system 18, the particle accelerator 11, delivery device 14 operate in a controlled manner such that the parameters of the particle beam to be delivered to the target including the energy, the intensity, and size and/or shape of the beam are modulated and dynamically controlled based on the treatment plan. The control system 18 also receives feedback signals from particle accelerator 11, beam delivery device 14, and supporting device 16 and generates tracking signals in response thereto.

For example, for a beam delivery system 14A illustrated in FIG. 2A where scattering media is used, the energy of the particle beam may be changed by controlling the accelerator 11 operation parameters so that the energy of the particle beam exiting the accelerator 11 is modulated based on the treatment plan. Alternatively, the energy of the particle beam extracted from the accelerator 11 may be changed by controlling the thickness of the energy degrader disposed along the beam path 12 according to the treatment plan. The beam energy may further be modulated by controlling the energy modifier 24A in the beam delivery device 14A. The energy modifier 24A may be shifters, wheels, wedges, or filters such as spread-out Bragg peak (SOBP) filters. To change the intensity of the particle beam, the accelerator 11 such as a cyclotron or synchrotron can be detuned so that some of the beam is not extracted. The slits on the beam path 12 can also be controlled to cut down the beam intensity. For linear accelerator, the accelerated beam pulse width can be adjusted to change the beam intensity. The lateral size of the particle beam may be changed by controlling the strength of the magnetic focusing fields, the size, shape and position of a multi-leaf collimator 28A, the thickness or materials of one or more scattering media 22A, 23A.

For a beam delivery system 14B illustrated in FIG. 2B where wobbling magnets 21B are used, the treatment control system 18 controls the energy or the intensity of the particle beam in a similar manner as in the embodiment illustrated in FIG. 2A. To control the lateral size of the particle beam, the control system 18 may change the strength of the magnetic focusing fields, and the size, shape and position of a multi-leaf collimator 28. Furthermore, the strength of the vertical and horizontal magnetic coils may be controlled to change the lateral size of the particle beam. An optional scattering media 22B may be used upstream the wobbling magnets 21B, and the thickness and materials of the scattering media 22B may be chosen to further enhance the lateral spreading of the particle beam.

For a beam delivery system 14C illustrated in FIG. 2C where scanning magnets 20C are used to scan a pencil beam, the treatment control system 18 modulates the energy or intensity of the particle beam in a similar manner as in the embodiments illustrated in FIGS. 2A and 2B. To control the lateral size of the particle beam, the control system 18 may change the magnetic focusing fields and the magnetic fields associated with pencil beam scanning.

The control system 18 further controls the rotation of the beam delivery device 14 or the gantry to which the delivery device 14 is mounted. The control system 18 also controls the motion of the supporting device 16 such as a treatment couch or chair on which the patient is supported. The control system 18 is also configured to receive signals from the rotating delivery device 14 and supporting device 16 and generates tracking signals in response thereto.

The patient treatment plan is established based on the nature, size, shape, and location of the target in the patient. The treatment plan includes data of the location and orientation of the target with respect to the coordinates of the radiation system established in a pre-treatment session. The treatment plan preferably includes data regarding the radiation doses different portions of the target should receive. Typically, the treatment plan sets forth several treatment sessions or fractions, and includes data regarding the energy, intensity, and the shape of the radiation beam and the time duration the radiation beam should be applied to the target at plurality of fields during a treatment session. By applying radiation at a plurality of fields, with the energy, intensity, and shape of the beam optimized to account for the shape of the target and other anatomical factors, a conformal dose is delivered.

In an intensity-modulated proton therapy (IMPT), the treatment plan further includes data regarding the motions of the leaves of the multi-leaf collimator for each field in the treatment session to achieve intensity-modulated radiation therapy. When each field is being executed, the multiple leaves in MLC beam adjuster move according to the IMRT plan so that different portions of the tumor's cross-section receive different amounts of radiation. For example, if one part of the tumor is close to a critical or sensitive structure, the leaves in the MLC beam adjuster may block the radiation near that part during some portion of the field, thereby decreasing the radiation dose received by that part of the tumor and minimizing the possible adverse effect of the radiation exposure by the critical or sensitive structure. The treatment plan may include data regarding particle beam scanning or modulation, or motions of MLC leaves for each field in the treatment session to achieve intensity-modulated proton therapy.

The treatment plan may also include reference data regarding the position of the target, and the relationship between the target movement and the patient's inter- or intra-fraction movement established during a pre-treatment session for image-guided radiation therapy (IGRT). The reference data or the relationship data can be obtained by any suitable imaging techniques such as planar radiography, ultrasound (US), computed tomography (CT), single photon emission computed tomography (SPECT), magnetic resonance imaging (MRI), magnetic resonance spectroscopy (MRS), positron emission tomography (PET), etc. In image-guided radiation therapy, the control module receives data from one or more planar or volumetric imaging devices representing near real time images of the target. The near real time image data are compared with the reference data obtained in the pre-treatment session. The results can then be used to position the patient and/or the radiation source during the treatment session. U.S. Pat. No. 7,227,925 describes a method and system for image-guided radiation therapy, the disclosure of which is incorporated herein by reference in its entirety.

Figure 3:
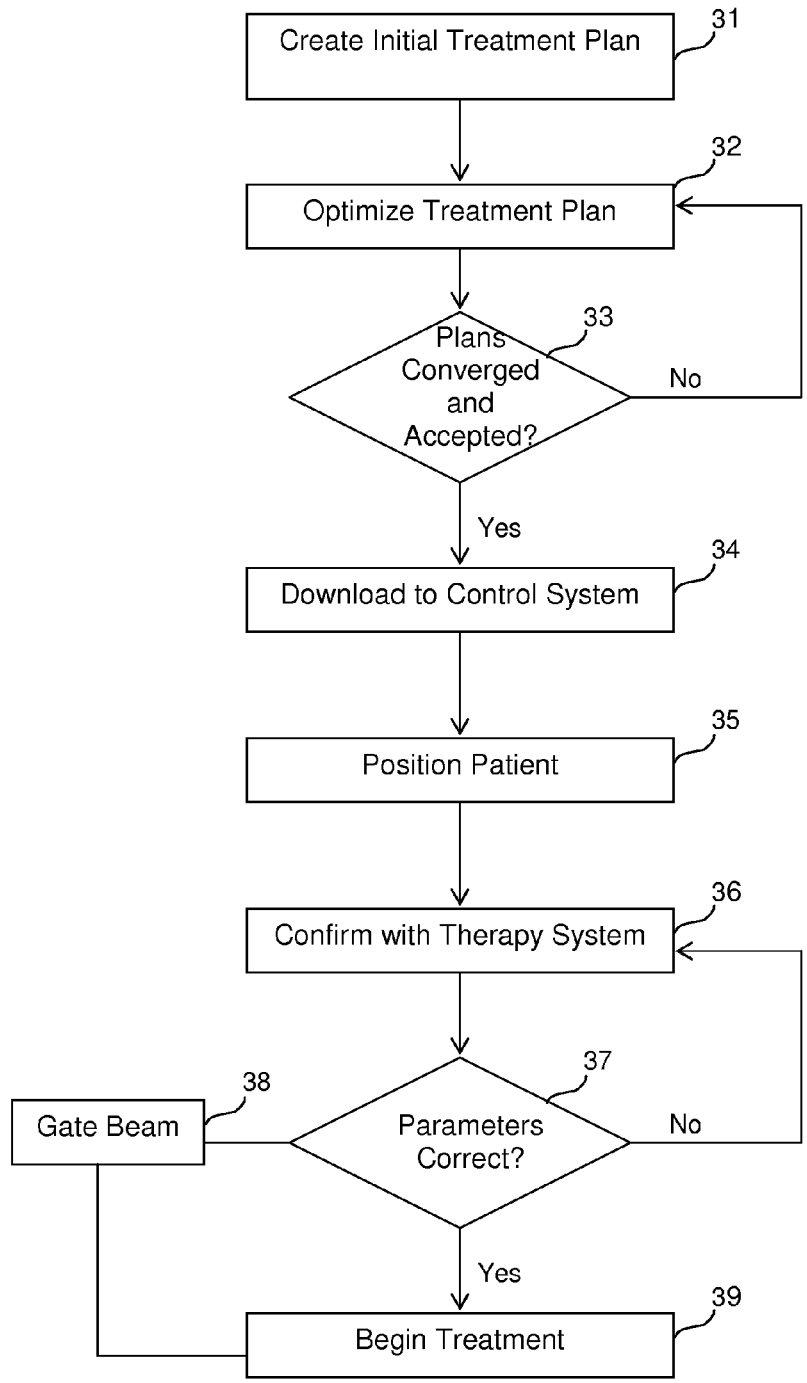
FIG. 3 is a flow chart illustrating a charged particle therapy method in accordance with one embodiment of the invention.

FIG. 3 is a flow chart illustrating a method for charged particle therapy in accordance with some embodiments of the invention.

An initial treatment plan is established using a treatment planning software based on the information about the individual patient. The patient information includes the nature, location, the size and shape of the tumor, which may be obtained by any suitable imaging techniques including computed tomography (CT), single photon emission computed tomography (SPECT), magnetic resonance imaging (MRI), magnetic resonance spectroscopy (MRS), positron emission tomography (PET), etc. The initial treatment plan includes data regarding the treatment doses different portions of the target should receive.

After the initial plan is created (step 31), the initial plan is optimized using a treatment optimizer or optimizing software for charged particle therapy at step 32. The treatment optimizer (to be described in more detail in FIG. 4) examines the parameters of the particle therapy system, including the accelerator system constraints, motion of the patient supporting device, rotation of the beam delivery device or the gantry including the delivery device, and various components such as energy modifiers, scatterers, wobbling and scanning magnets, collimators etc., to find an optimal treatment plan. One goal of the optimization of the treatment plan is to find an optimal treatment plan for improved dose conformity in a gantry rotation or continuous gantry rotation, or a single gantry rotation in 360 degrees subject to the constraints from the initial treatment plan and the accelerator systems.

The optimized treatment plan is evaluated at step 33 to determine if the optimized plan is converged with the initial treatment plan. If not, the flow returns to step 32 for continuing optimization. If yes, the treatment plan is approved, stored, and downloaded to the treatment control system at step 34.

At step 35, the patient is positioned on the supporting device. Particle therapy system parameters are requested at step 36 to determine if the system parameters confirm with the parameters of the approved treatment plan at step 37. If one or more of the system parameters are confirmed to be incorrect, the treatment is fault stopped. The particle therapy system is adjusted and the flow returns to step 37 for further parameter confirmation.

If all system parameters are confirmed to be correct, treatment begins at step 39. The energy, the intensity, and the size and shape of the charged particle beam are dynamically modulated or changed as the gantry rotates and/or as the supporting device moves, based on the treatment plan. The treatment may end in one or two gantry rotations, or in a partial gantry rotation.

Figure 4:
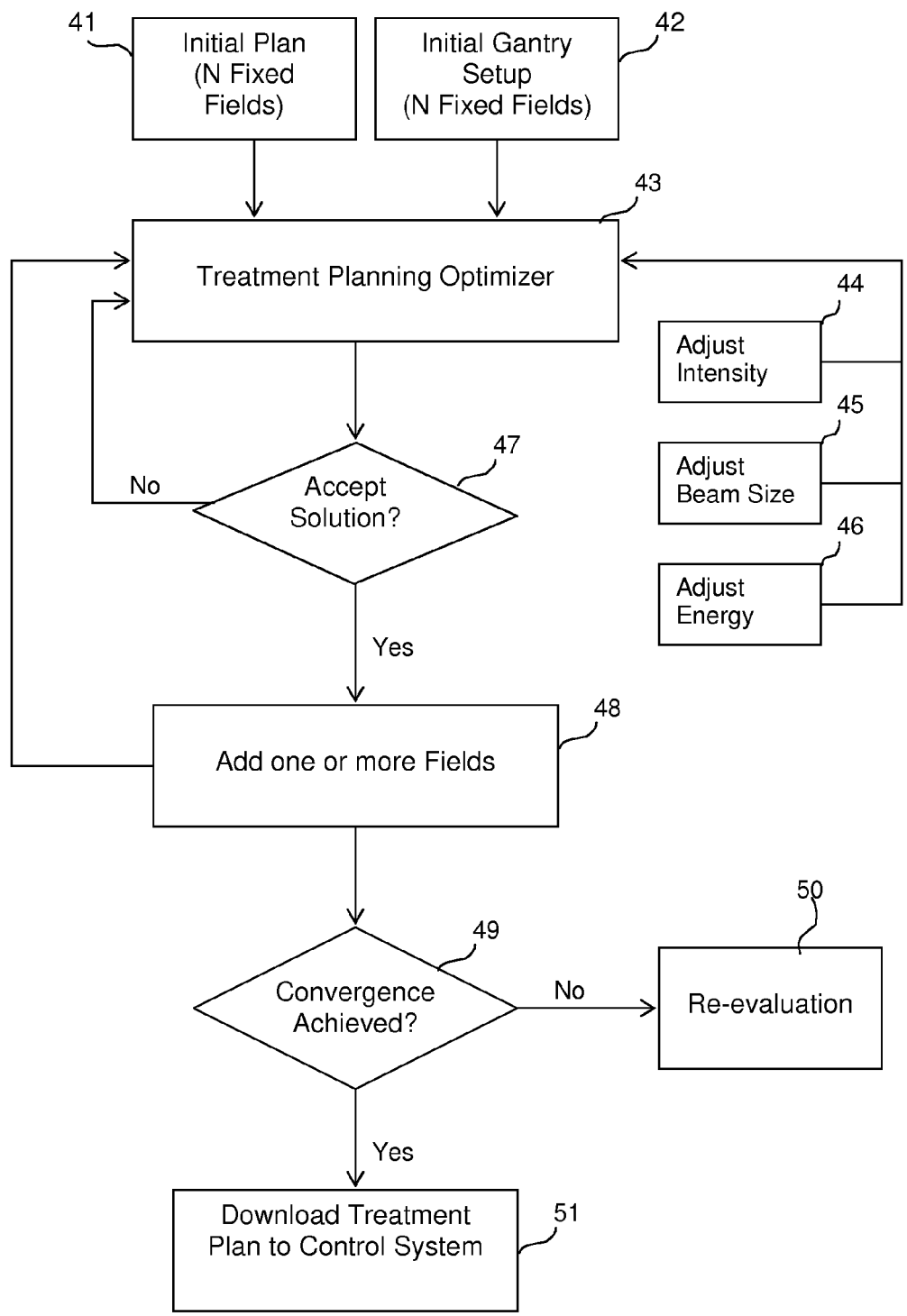
FIG. 4 is a flow chart illustrating a method of optimizing a charged particle therapy method in accordance with one embodiment of the invention.

FIG. 4 is a flow chart illustrating the function of a treatment planning optimizer in accordance with some embodiments of the invention.

The process begins at step 41 and 42 with inputting to the treatment planning optimizer an initial treatment plan with fixed IMRT fields (e.g. N fields) and information data on patient's supporting device and gantry with fixed fields corresponding to the initial treatment plan. The treatment optimizer then examines the parameters of the particle therapy system to optimize the treatment plan at step 43.

The parameters to be examined include but are not limited to those that modulate the energy, intensity, and the size of the particle beam. For example, to adjust the intensity of the particle beam at step 44, the ion source, the accelerator, the scattering media, SOBP filters, and collimators such as MLC can be changed. To adjust particle beam size at step 45, the strength of the magnetic focusing fields, the size, shape and position of a multi-leaf collimator, the thickness or materials of one or more scattering media can be changed. To adjust the energy of the charged particle beam at step 46, the accelerator system (tuning and extraction), the beam path (energy degraders such as wedges or wheels), and beam delivery device (energy modifiers or SOBP filters) can be changed.

At step 47, a solution involving the system parameters is examined to determine if it is acceptable in light of the initial treatment plan. If not, the flow returns to the treatment planning optimizer 43 to further adjust the system parameters. If the solution is acceptable, the flow goes to step 48 where one or more radiation fields or gantry positions are added. The added fields may be uniformly distributed around the initial fields. Then the process calls the treatment planning optimizer 43, and loops until the convergence is achieved. The goal is to achieve the maximal dose conformity to the target tumor with minimal treatment margins, spare the healthy tissue and critical organs, and all system parameters are within the operation range.

At step 49, the solution to the treatment plan is examined to determine if it is acceptable. If not, the flow proceeds to step 50 to evaluate the reasons for non-convergence. If the solution is acceptable, the optimized treatment plan is stored, downloaded to the control system at step 51 for the particle beam therapy execution.

A method of treating patient tumors using charged particle therapy has been described. The system parameters are actively controlled in the delivery of charged particles in such a way that the treatment time is minimized and the accuracy of radiation delivery is increased. As a result, the dose delivered to the tumor site is more accurate and the dose to nearby tissues and critical structures is minimized.

From the foregoing it will be appreciated that, although specific embodiments of the invention have been described herein for purposes of illustration, various modifications may be made without deviating from the spirit and scope of the invention. For instance, a gating process 38 (FIG. 3) may be incorporated in the process of particle therapy. For example, the control system may generate a signal to momentarily shut down the particle source in response to sudden movement of the patient in an abnormal pattern, such as coughing, sneezing, muscle cramping etc. When the tumor resumes its normal movement, e.g., the periodic movement associated with the breathing of the patient, the control system may turn the particle source back on, permitting the radiation on the patient. All these or other variations and modifications are contemplated by the inventors and within the scope of the invention.

What is claimed is:

1. A method of irradiating a target in a subject, comprising the steps of:
    positioning a subject on a supporting device;
    positioning a delivery device adapted to deliver charged particles; and
    delivering charged particles to a target in the subject, wherein the delivery device is in motion and rotates around the target while at least some of the charged particles are delivered, and one or more parameters of the charged particles are modulated when the delivery device is in motion, said parameters including the energy, the intensity, and the beam direction of the charged particles.

2. The method of claim 1 wherein two or more parameters including the energy, the intensity, the beam direction and the beam shape of the charged particles are concurrently modulated when the delivery device is in motion.

3. The method of claim 1 wherein in the delivering step a multi-leaf collimator is used to shape and modulate the energy of the charged particles concurrently.

4. The method of claim 1 wherein said delivery device is mounted to a gantry capable of rotating in 360 degrees or more.

5. The method of claim 1 wherein in the delivering step the supporting device is concurrently moved.

6. The method of claim 1 wherein the charged particles are protons.

7. A radiation method comprising:
    positioning a subject on a supporting device;
    positioning a delivery device adapted to deliver charged particles; and
    delivering charged particles to a target in the subject, wherein the delivery device is in motion while at least some of the charged particles are delivered, and wherein all or substantially all of charged particles for a treatment fraction are delivered to the target during a single rotation of the delivery device in about 360 degrees or less.

8. A method of irradiating a target in a subject, comprising the steps of:
    positioning a subject on a supporting device;
    positioning a delivery device adapted to deliver charged particles; and
    delivering charged particles to a target in the subject, wherein the energy of the charged particles is modulated such that the Bragg peaks of the charged particles are deposited approximately on the distal periphery of the target, and the delivery device is in motion while at least some of the charged particles are delivered.

9. The method of claim 8 wherein in the delivering step the delivery device is stationary during delivery of at least a portion of the charged particles.

10. The method of claim 8 wherein the charged particles are in the form of a pencil beam.

11. The method of claim 8 wherein the charged particles are protons.

12. The method of claim 8 wherein in the delivering step the energy and the intensity of the charged particles are concurrently modulated.

13. The method of claim 8 wherein in the delivering step all or substantially all charged particles for a treatment fraction are delivered to the target during a single rotation of the delivery device in about 360 degrees or less.

14. The method of claim 8 wherein in the delivering step the supporting device is concurrently moved.

15. The method of claim 8 further comprising the step of gating the delivery of charged particles in response to abnormal or normal movement of the subject.

16. A charged particle therapy system comprising:
    a particle accelerator;
    a particle delivery device; and
    a beam path for transporting charged particles generated by the particle accelerator to the delivery device;
    wherein said delivery device is configured to rotate around a target and be in motion while at least some of the charged particles are delivered in operation, and said delivery device comprises a multi-leaf collimator configured to shape and modulate the energy of the particles concurrently.

17. The system of claim 16 wherein the delivery device is coupled to a gantry rotatable in 360 degrees or more.

18. The system of claim 16 wherein said multi-leaf collimator is configured to shape and scatter the charged particles concurrently.

19. The system of claim 16 wherein said multi-leaf collimator is a 3-dimensional multi-leaf collimator.

20. A method of irradiating a target in a subject, comprising the steps of:
    positioning a subject on a supporting device;
    positioning a delivery device adapted to deliver charged particles; and
    delivering charged particles for a treatment fraction to a target in the subject using the delivery device with more than one rotations, wherein in a first rotation, the Bragg peaks of substantially all charged particles are deposited approximately on the distal periphery of the target, and in a second rotation, the Bragg peaks of substantially all charged particles are deposited approximately in the interior of the target.

21. The method of claim 20 wherein the delivery device is in motion while at least some of the charged particles are delivered.

22. The method of claim 20 wherein one or more parameters of the charged particles are modulated when the delivery device is in motion, said parameters including the energy, the intensity, the beam direction and the beam shape of the charged particles.

23. The method of claim 20 wherein two or more parameters including the energy, the intensity, the beam direction and the beam shape of the charged particles are concurrently modulated when the delivery device is in motion.

24. The method of claim 20 wherein said first or second rotation is a complete rotation in about 360 degrees or a partial rotation less than 360 degrees.

25. The method of claim 20 wherein the charged particles are delivered to the target at selected angles of rotations.

26. The method of claim 20 further comprising the step of gating the delivery of charged particles in response to abnormal or normal movement of the subject.

27. A radiation method comprising:
positioning a subject on a supporting device;
positioning a delivery device adapted to deliver charged particles; and
delivering charged particles to a target in the subject, wherein the delivery device is in motion and rotates around the target while at least some of the charged particles are delivered; and
gating the delivery of charged particles in response to abnormal or normal movement of the subject.

28. A charged particle therapy system comprising:
a particle accelerator configured to generate charged particles;
a delivery device, said delivery device is rotatable and configured to be in motion while at least some of the charged particles are delivered in operation
a beam path for transporting charged particles from the particle accelerator to the delivery device; and
a control system configured to gate the delivery of charged particles in response to abnormal or normal movement of the target.

29. A radiation method comprising:
positioning a subject on a supporting device;
positioning a delivery device adapted to deliver protons or heavy ions; and
delivering protons or heavy ions to a target in the subject, wherein the delivery device is in motion and rotates around the target while at least some protons or heavy ions are delivered.

30. A charged particle therapy system comprising:
a particle accelerator configured to generate protons or heavy ions;
a delivery device; and
a beam path for transporting protons or heavy ions generated by the particle accelerator to the delivery device;
wherein said delivery device is rotatable and configured to be in motion while at least some protons or heavy ions are delivered in operation.

* * * * *